United States Patent
Mougin

(10) Patent No.: US 6,690,453 B2
(45) Date of Patent: Feb. 10, 2004

(54) METHOD AND DEVICE FOR PREDICTING THE FLOCCULATION THRESHOLD OF ASPHALTENES CONTAINED IN HYDROCARBON MIXTURES

(75) Inventor: Pascal Mougin, Rueil-Malmaison (FR)

(73) Assignee: Institut Francais du Petrole, Reuil-Malmaison Cedex (FR)

( * ) Notice: Subject to any disclaimer, the term of this patent is extended or adjusted under 35 U.S.C. 154(b) by 0 days.

(21) Appl. No.: 10/067,232

(22) Filed: Feb. 7, 2002

(65) Prior Publication Data
US 2002/0140925 A1 Oct. 3, 2002

(30) Foreign Application Priority Data
Feb. 7, 2001 (FR) .......................................... 01 01750

(51) Int. Cl.$^7$ ............................................... G01N 33/26
(52) U.S. Cl. ........................................ 356/70; 250/301
(58) Field of Search ............................ 356/70; 250/301

(56) References Cited

U.S. PATENT DOCUMENTS

| | | | |
|---|---|---|---|
| 4,628,204 A | | 12/1986 | Maes |
| 5,034,807 A | * | 7/1991 | Von Kohorn .................... 725/5 |
| 5,420,040 A | * | 5/1995 | Anfindsen et al. ............. 436/60 |
| 5,715,046 A | | 2/1998 | Tolvanen |
| 6,087,662 A | * | 7/2000 | Wilt et al. .............. 250/339.12 |

FOREIGN PATENT DOCUMENTS

| | | |
|---|---|---|
| EP | 0304233 | 2/1989 |
| FR | 2578979 | 9/1986 |
| FR | 2647903 | 12/1990 |
| WO | 0 892 268 A1 * 1/1998 | ......... G01N/31/16 |

\* cited by examiner

Primary Examiner—Zandra V. Smith
Assistant Examiner—Kara Geisel
(74) Attorney, Agent, or Firm—Antonelli, Terry, Stout, & Kraus, LLP

(57) ABSTRACT

Method and device for predicting the flocculation threshold of asphaltenes contained in hydrocarbon mixtures.

The method comprises the following stages:
- determining the refraction index ($n_A$) of several asphaltenes used as reference asphaltenes;
- determining experimentally, for predetermined thermodynamic conditions, the variation of solubility index ($\delta$) in connection with the refraction index of hydrocarbon constituents including light hydrocarbons and reference asphaltenes;
- deducing therefrom a correlation relation modelling this variation of solubility index ($\delta$).

These preliminary operations being performed,
- refraction index ($n_A$) of the asphaltenes of the hydrocarbon mixture is determined under the same thermodynamic conditions and by reference to said correlation relation, solubility index ($\delta$) of the asphaltenes of said mixture is deduced therefrom; and
- from the solubility index of the asphaltenes of said mixture and from a thermodynamic equilibrium model, the flocculation threshold thereof is directly predicted.

Applications: fast laboratory determination of asphaltene flocculation risks likely to hinder production and transport of crudes so as to quickly implement solutions intended to prevent them.

5 Claims, 4 Drawing Sheets

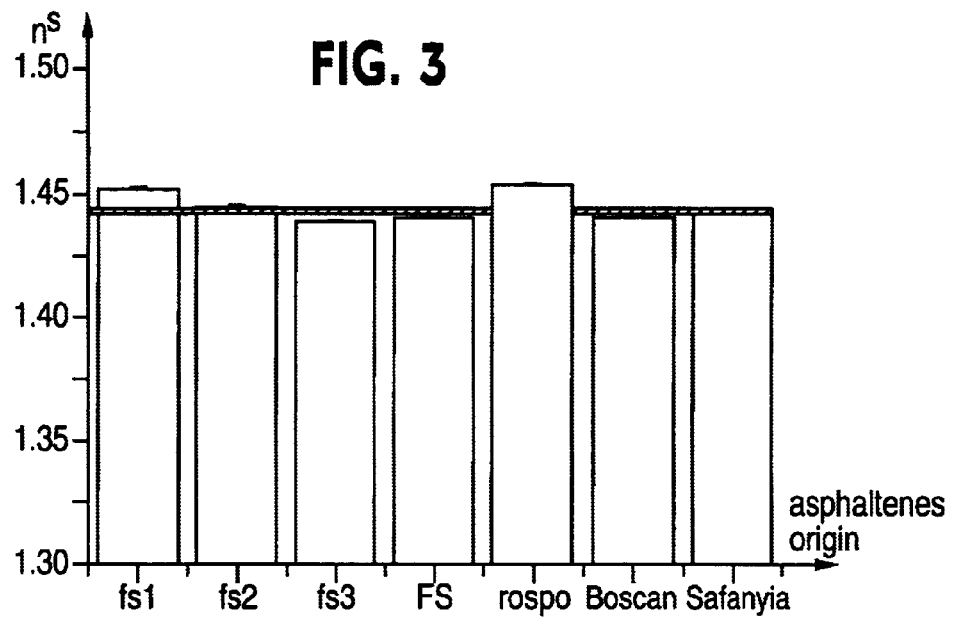
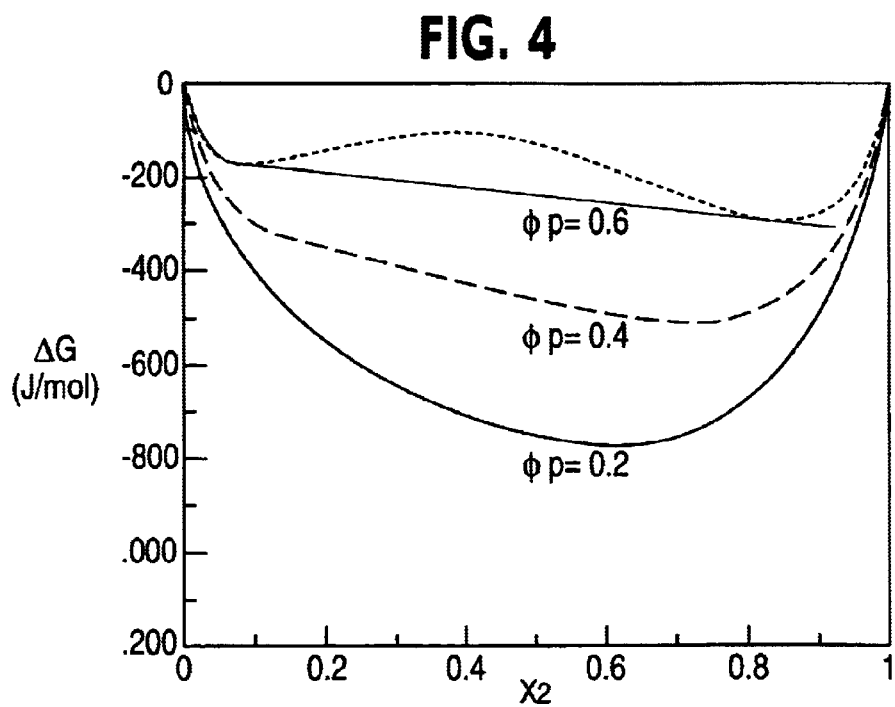

METHOD AND DEVICE FOR PREDICTING THE FLOCCULATION THRESHOLD OF ASPHALTENES CONTAINED IN HYDROCARBON MIXTURES

FIELD OF THE INVENTION

The present invention relates to a method and to a device allowing fast prediction of the flocculation threshold of asphaltenes from the measurement of their optical refraction index.

The method finds applications notably in the production or the transport of petroleum products for predicting the flocculation of asphaltenes and for fighting it by means of various processes.

During extraction or transport, crudes are subjected to temperature, pressure, shear variations, and to operations modifying the composition thereof. These modifications can lead to the flocculation of heavy constituents of crude oils such as asphaltenes. As this precipitate does not redissolve spontaneously, it can eventually, as it accumulates, clog lines, part of the porous matrix of the formation or a catalyst grain. The deposits resulting from the precipitation of asphaltenes are the main causes of servicing operations during processing of the petroleum chain It is therefore necessary to be able to predict in time the flocculation of asphaltenes in order to prevent or to fight it.

BACKGROUND OF THE INVENTION

Measurement of the flocculation threshold consists in adding progressively to an asphaltene solution a flocculant that can be, according to standards, pentane, heptane, etc. The following methods can be distinguished:

a) a test referred to as spot test: the flocculated asphaltenes do not diffuse as quickly as the surrounding liquid when the mixture is deposited on a filter paper. A uniform spot corresponds to an absence of flocculated asphaltenes, whereas a black area in the middle of the spot corresponds to a flocculation;

b) an optical method by light diffusion in the near infrared allowing continuous and in-situ monitoring of the appearance of the threshold, as described for example in patent FR-2,647,903 filed by the applicant. This threshold is defined as the minimum amount of flocculant to be added to the solution for the formation of the first asphaltene aggregates to be observed.

Other techniques have been developed since then: light diffusion (UV and visible), particles size, gravimetric analysis, optical fluorescence, viscosity, electrical conductivity, thermal conductivity analysis. They are all based on the same principle: the addition of flocculant leads to two effects: dilution of the sample and increase in the size of the aggregates. Below this threshold, the dilution effect prevails. Crossing the threshold leads to a great increase in the size of the aggregates and this effect prevails over dilution.

A possible method of determining the flocculation threshold consists in preparing at the time $_0$ different solutions of asphaltenes in toluene to which various heptane concentrations are added for example. Immediately afterwards (at $t_0+1$ mn for example), its refraction index is measured by means of a refractometer of a well-known type. The Abbe refractometer is for example used, whose principle essentially consists in measuring the critical angle of total refraction of a light beam falling on a diopter consisting of a sapphire prism, of high index (1.7), and of the sample to be measured.

The diopter thus obtained is <<lit>> by a light source having an angular distribution that allows to reach all of the incidences corresponding to the limits of the measurement range accessible by the device. Then, after a predetermined time interval ($t_0+5$ mn for example, according to the experimental protocol selected), the various solutions are examined under the microscope to see if the asphaltenes flocculate (see FIG. 1). It is well-known that the polarizability of a mixture of constituents, under certain hypotheses, is the sum of the contributions of each one of the fractions that constitute this mixture. If the mixture volumes are ideal (without excess volume), if there is no chemical reaction when the constituents are mixed and if the disturbances of the individual oscillators, linked with the presence of neighbours of different chemical nature are not too great, the number of atoms of each constituent per total volume unit being denoted by $N_j$, we can write the Clausius-Mosotti $$3\frac{n^2-1}{n^2+2} = \sum_j N_j \alpha_j \tag{1}$$

equation:

where $\alpha_j$ is the polarizability of constituent j.

We therefore draw (FIG. 2) the variation curve of function $$\left(n_s = \frac{n^2-1}{n^2+2}\right),$$

of refraction index n as a function, on the abscissa, of the volume fraction of the titrant of the mixture (1–Φ) (Φ heptane volume fraction of the various solutions) and the first point for which a flocculation onset is observed is located on the curve obtained. The value of the refraction index at this point represents the refraction index $n_{SF}$ at the flocculation threshold. The lower volume fraction Φ, the more the asphaltene will tend to flocculate. The asphaltene flocculation risk therefore varies in inverse proportion to Φ.

In order to be accurate, this known method requires comparative examination of a great number of solutions with different heptane titers, and consequently a longer experimentation time.

On the other hand, Wang J. et al describe, in: <<Improved Modeling of the Onset of Asphaltene Flocculation >>, $2^{nd}$ International Conference on Petroleum & Gas Phase Behavior and Fouling, Copenhagen, August 2000, a modelling method wherein asphaltene solutions are considered as a binary mixture of a solvent (maltenes) and of a solute (asphaltenes), and a Flory-Huggins type model, well-known to specialists, is used to predict their flocculation. The free enthalpy of mixing $\Delta G_m$ is given by the relation as follows:

$$\Delta G_m = \Delta H_m - T\Delta S_m \tag{2}$$

The entropy term is the Flory-Huggins terms involving the molar fractions (x) and the volume fractions (ϕ):

$$\Delta S_m = -R(x_1 \ln\phi_1 + x_2 \ln\phi_2) \tag{3}$$

On the other hand, the enthalpy term involves the solubility parameters of the solvent and of the solute through interaction parameter χ:

$$\Delta H_m = RTx_1\phi_2\chi \tag{4}$$

$$\chi = \frac{v_1}{RT}(\delta_2 - \delta_1)^2 \qquad (5)$$

In these expressions, subscripts 1 and 2 correspond to the solvent and to the solute respectively. Interaction parameter $\chi$ involves Hildebrand's solubility parameters $\delta$. Now, these parameters are defined from the cohesive-energy densities. $\delta_1$ and $\delta_2$ are therefore measurements of the cohesive energies of the solvent and of the asphaltene aggregates respectively. The expression of the free enthalpy of mixing allows to determine the chemical potentials of the two species (solvent and solute). The flocculation of asphaltenes is then dealt with conventionally like a phase separation.

When modelling an addition of flocculant nC7 for example, the parameters relative to the solvent, $(\delta_1, v_1)$ and the molar fractions of solvent and of solute, are modified. In doing so, the free enthalpy curve is modified (see FIG. 4). For low proportions of flocculant ($\Phi_p$), the free enthalpy is concave at any point and no phase separation is favourable from the viewpoint of energy. On the other hand, with high proportions of flocculant, the free enthalpy has a convex domain and a phase separation occurs. A tangent to the curve can in fact be drawn, which gives two mixtures at phase equilibrium. The model thus allows, knowing the quality of the solvent, to define whether the system is stable or if there is a phase separation.

In this model, the flocculation threshold is defined as the case in which the free enthalpy curve goes from a concave to a convex situation. In other words, we change from a single-phase stable system to a two-phase system. This leads to the appearance of a zero-tangent flex point on the free enthalpy curve. Mathematically, by using the chemical potentials of the two species, we can write:

$$\ln(1-\phi_2) + \left(1 - \frac{1}{m}\right)\phi_2 + \chi(\phi_2)^2 = \qquad (6)$$
$$\ln(\phi_2) + (1-m)(1-\phi_2) + m\chi(1-\phi_2)^2$$

where m is the ratio of the molar volumes of the solute and of the solvent.

However, the predictions that could be made by means of Wang et al's modelling method to connect the solubility parameter $\delta$ of the asphaltenes to the refraction index function do not really match the experimental results that can be obtained.

SUMMARY OF THE INVENTION

The method according to the invention allows fast prediction of the flocculation threshold of asphaltenes contained in hydrocarbon mixtures. It comprises the following stages:
  determining the refraction index ($n_A$) of several asphaltenes used as reference asphaltenes;
  determining expermnentally, for predetermined thermodynamic conditions, the variation of solubility index ($\delta$) in connection with the refraction index of hydrocarbon constituents including light hydrocarbons and reference asphaltenes;
  deducing therefrom a correlation relation modelling this variation of solubility index ($\delta$).
  These preliminary operations being performed,
  refraction index ($n_A$) of the asphaltenes of the hydrocarbon mixture is determined under the same thermodynamic conditions and by reference to said correlation relation, solubility index ($\delta$) of the asphaltenes of said mixture is deduced therefrom; and from the solubility index of the asphaltenes of said mixture and from a thermodynamic equilibrium model, the flocculation threshold thereof is directly predicted.

The variation of refraction index ($n_A$) can be determined for example by extrapolation from several measured refraction index values obtained for several solutions with relatively low concentrations of these asphaltenes in solvents.

The device according to the invention allows to predict the flocculation threshold of asphaltenes contained in a given hydrocarbon mixture. It comprises a refractometer and a system suited to experimentally determine, under predetermined thermodynamic conditions, the refraction index ($n_A$) of asphaltenes, to determine the variations of solubility index ($\delta$) in connection with variations of the refraction index of known hydrocarbon constituents including light hydrocarbons and several known reference asphaltenes, to deduce therefrom a correlation relation modelling these variations of solubility index ($\delta$) and to apply this correlation relation to a thermodynamic equilibrium model so as to directly predict the flocculation threshold of the asphaltenes contained in said hydrocarbon mixture.

The system comprises at least a programmed computer and, in some cases, an equipment for bringing asphaltenes into solution in a solvent at variable concentrations.

BRIEF DESCRIPTION OF THE FIGURES

Other features and advantages of the method and of the device according to the invention will be clear from reading the description hereafter of non-limitative examples, with reference to the accompanying drawings wherein:

is represented as a function of the volume fraction of titrant of the mixture: $\phi$ (heptane), examination under the optical microscope allowing to know if the sample is homogeneous (○) or flocculated (●), FIG. 3 shows the variations of the refraction index for various types of asphaltenes studied, FIG. 4 shows the variations of the free enthalpy of mixing.

DETAILED DESCRIPTION

Figure 1:
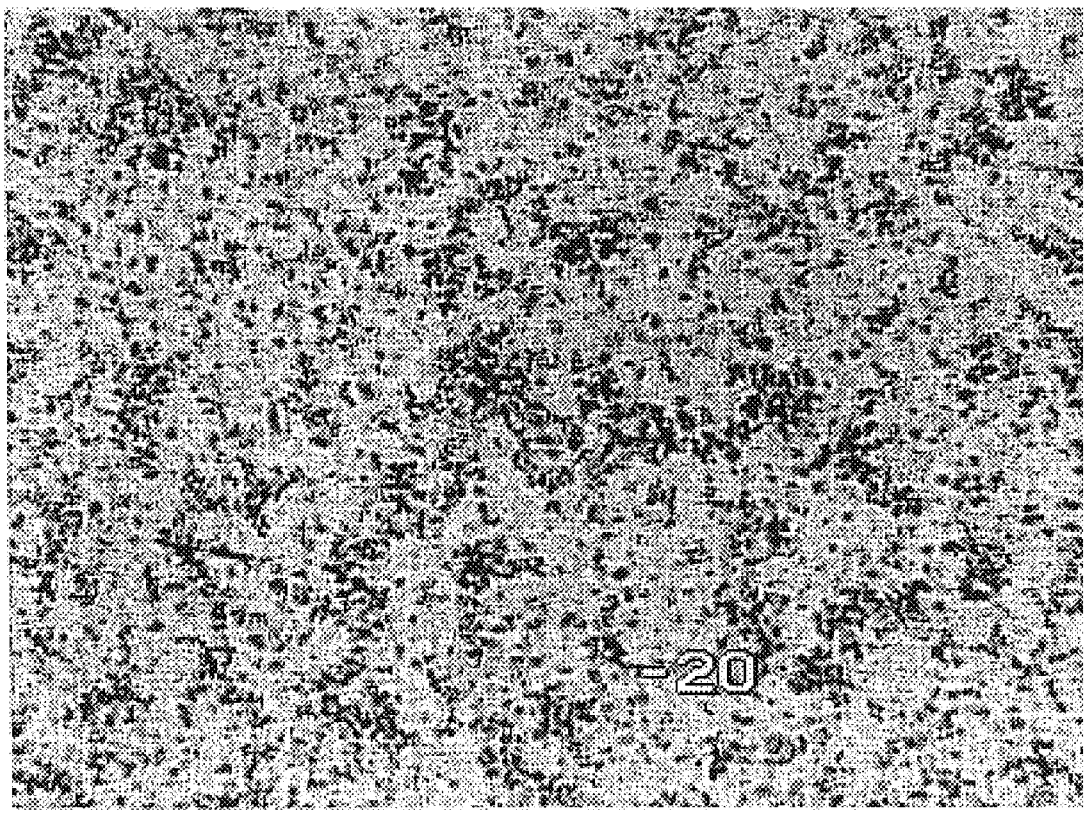
FIG. 1 shows an optical microscopy photograph of a solution of asphaltenes in a mixture of toluene and heptane on the flocculation threshold.

The method according to the invention first comprises determining the refraction index of asphaltenes for several different values of the volume fraction $\Phi$ of asphaltenes in a solvent such as toluene. The variation curve (substantially linear) as a function of $\Phi$ is drawn for at least some low values of $\Phi$, as far as allowed by the refractometer used. In fact, a conventional optical refractometer such as Abbe's refractometer has its limitations as regards analysis of highly absorbent black media such as asphaltene solutions for relatively high values of Φ. It is therefore necessary to multiply the measuring points to improve the accuracy and therefore the dilutions to be made. The refraction index being sensitive to the temperature (dn/dT is of the order of about $10^{-4}$ URI/° C.), all the measurements are performed at a controlled temperature of 28° C. for example. Determination of $n_A$ is carried out by extrapolation to 100% asphaltenes of the least squares regression line. As shown in FIG. 1, the measured concentrations are below 5% by weight of asphaltenes. The confidence interval as regards the extrapolated value is relatively great and depends on:

the number of measuring points, the dispersion of the values around the mean line, the density of the asphaltenes assumed to be constant here.

The results concerning the refraction index of the asphaltenes of various origins are shown in FIG. 3.

Figure 5:
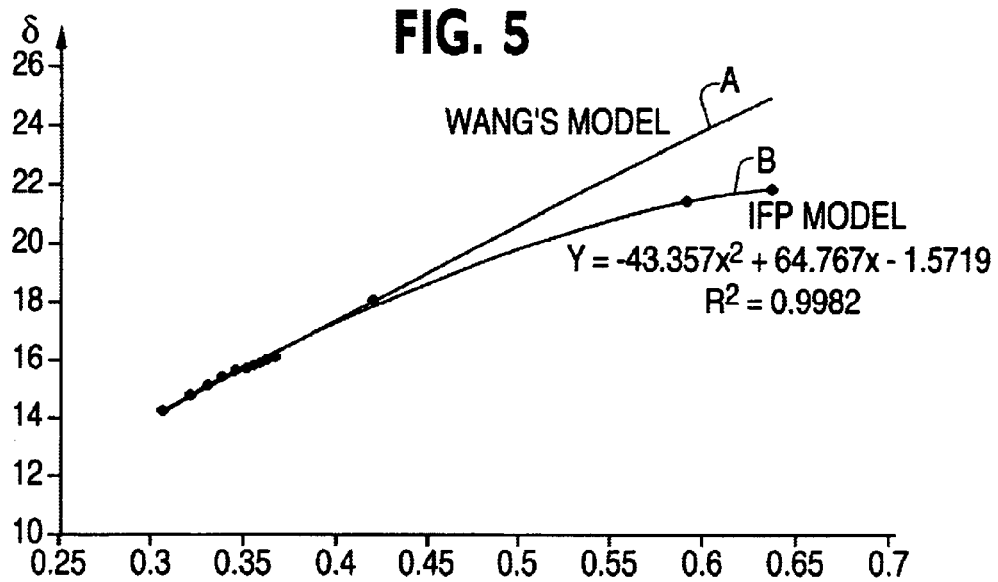
FIG. 5 shows the correlation existing between the solubility parameter and the refraction index according to Wang's model (curve A) and the model according to the invention (curve B)

The method according to the invention thereafter comprises determining a relation allowing to connect the variations of solubility parameter δ to relative refraction index $n_A$ and satisfying the experimental measurements for the light hydrocarbons: n-alkanes up to C10, known from the literature (part A of the curve of FIG. 5) as well as for the much heavier fractions whose refraction indices are significantly higher. After connecting the values of solubility parameter δ to refraction index $n_A$ for two asphaltene solutions for which we have adjusted the solubility parameters to the flocculation threshold measurements, we can draw the completed curve (part B of FIG. 5) for the variation curve of solubility parameter δ and establish a correlation relation that smoothes the data concerning n-alkanes, toluene and two asphaltenes:

$$\delta = -43.357 \left( \frac{n^2-1}{(n^2+2)^{3/4}} \right)^2 + 64.767 \left( \frac{n^2-1}{(n^2+2)^{3/4}} \right) - 1.5719$$

This relation is valid under certain predetermined thermodynamic conditions and it must of course be adjusted to the temperature and pressure conditions under which the asphaltenes are analyzed.

We then use this correlation relation to predict the flocculation thresholds of other asphaltene solutions.

Figure 6:
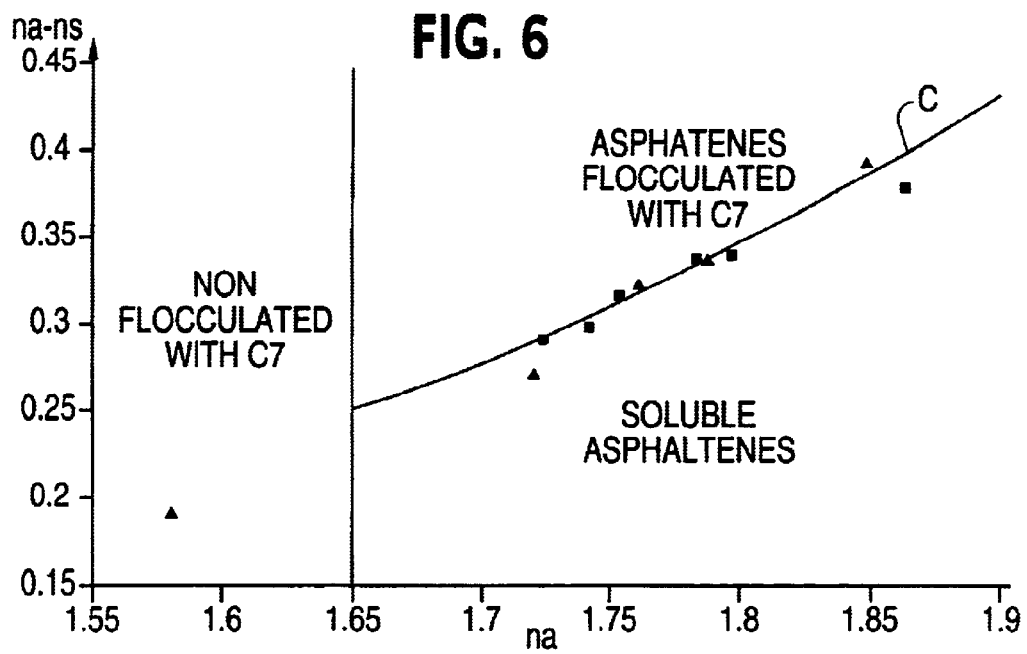
FIG. 6 shows a stability diagram of asphaltenes (1% by weight) of different nature in a good/bad solvent mixture whose proportions are given by Clausius-Mosotti's mixing law.
Figure 7:
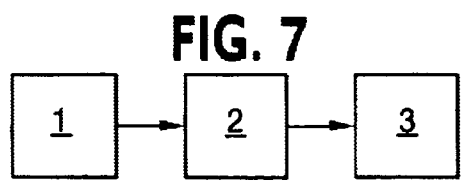
FIG. 7 is a block diagram of the device for implementing the method.

FIG. 6 shows the results in form of the difference between index $n_A$ of the asphaltenes and flocculation threshold index nSF as a function of index $n_A$ of the asphaltenes. The points represented by black squares are obtained by means of the expirimental method described in the prior art with examination of various solutions under the microscope to observe the flocculation of asphaltenes (see FIG. 10). Other points represented by black triangles come from the literature available in this field.

It can be seen that the modelling curve C obtained by applying the method corresponds very well to the various experimental points.

The variations thus modelled are used as input data in a thermodynamic equilibrium model such as Flory-Huggins' model, mentioned above, in order to directly predict the flocculation threshold of the asphaltenes in the asphaltene mixture studied. This curve also comprises the index of a resin (n~1.58) and it can be seen with the model that there is no flocculation of this resin with heptane. In fact, if the index of the asphaltenes is below 1.65, the model predicts no flocculation. The model being adjusted to two flocculation threshold measurements, the other experimental points are entirely predicted.

Figure 2:
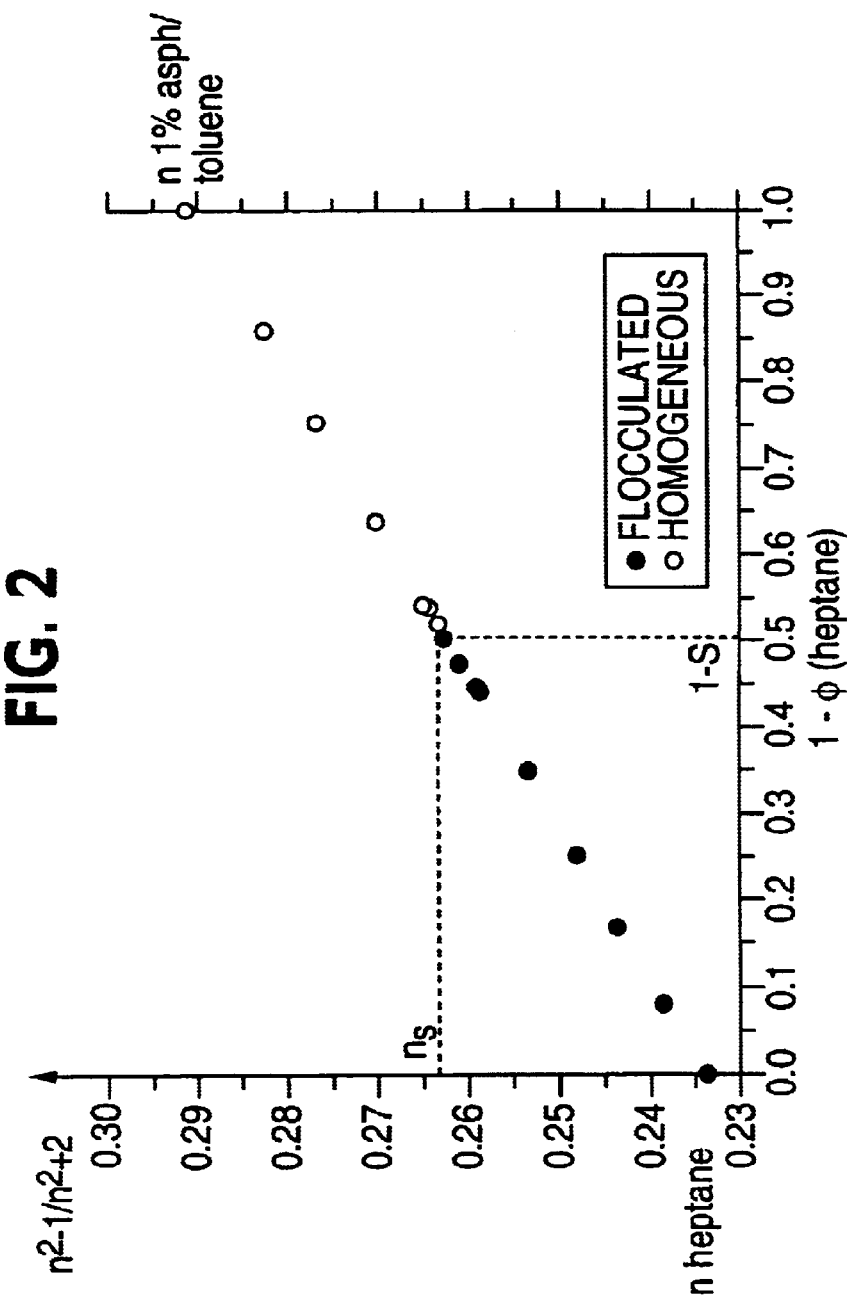
FIG. 2 shows a titration example in the case of a <<synthetic>> system where the relative index $$\frac{n^2 - 1}{n^2 + 2}$$

The device for implementing the method comprises a refractometer 2 of a well-known type (Abbe's refractometer for example) and a system including a computer or workstation 3 suited to:

experimentally determine by extrapolation (see FIG. 2), under predetermined thermodynamic conditions, the refraction index ($n_A$) of asphaltenes, determine the variations of the solubility index (δ) in connection with variations of the refraction index n of known hydrocarbon constituents including light hydrocarbons and of several known reference asphaltenes (cf. FIG. 5), deduce therefrom a correlation relation (19) modelling these variations of solubility index (δ) and to apply this correlation relation to a thermodynamic equilibrium model so as to directly predict the flocculation threshold of the asphaltenes contained in said hydrocarbon mixture.

Determination of the refraction indices requires, as mentioned above, determination of the slope of a line (see FIG. 2) lining various points corresponding to various volume fractions Φ.

When using a refractometer 2 capable of measuring solutions comprising a high volume fraction Φ (close to 0.5 for example), a single refraction index measurement can be sufficient because the point obtained is very far (see FIG. 2) from the point corresponding to the pure solvent (heptane for example) whose refraction index is known.

When the refractometer used only allows to measure low values of the volume fraction Φ in the solvent, the right value of the slope has to be found and the refraction index ($n_A$) measurements have to be repeated for high dilution ratios of the asphaltenes, different but close to one another. The device comprises in this case a dilution device 1 allowing to obtain various degrees (relatively low) of asphaltene concentration in the solvents so as to multiply the refraction index measurements.

Computer 3 is suited to determine the values of indices ($n_A$) of the asphaltenes from measurements provided by refractometer 2. It is also suited to determine the correlation relation modelling the connection between the solubility indices (δ) and variations of the refraction index, which will be used thereafter in order to directly determine the value of this solubility index (δ) of the asphaltenes in the mixtures to be studied under the same thermodynamic conditions.

What is claimed is:

1. A method for predicting the flocculation threshold of asphaltenes contained in a hydrocarbon mixture, characterized in that the following stages are carried out:

determining the refraction index ($n_A$) of several asphaltenes used as reference asphaltenes;

determining experimentally, for predetermined thermodynamic conditions, the variation of solubility index (δ) in connection with the refraction index of hydrocarbon constituents including light hydrocarbons and reference asphaltenes;

deducing therefrom a correlation relation modelling this variation of solubility index (δ).

determining refraction index ($n_A$) of the asphaltenes of the hydrocarbon mixture under the same thermodynamic conditions and by reference to said correlation relation, deducing solubility index (δ) of the asphaltenes of said mixture therefrom; and predicting directly the flocculation threshold from the solubility index of the asphaltenes of said mixture and from a thermodynamic equilibrium model.

2. A method as claimed in claim 1, characterized in that the variation of refraction index ($n_A$) is determined by extrapolation from measured refraction index values obtained for several solutions of relatively low concentration of these asphaltenes in solvents.

3. A device for predicting the flocculation threshold of asphaltenes contained in a given hydrocarbon mixture, characterized in that it comprises a refractometer (2) and a system (1, 3) suited to experimentally determine, under predetermined thermodynamic conditions, the refraction index ($n_A$) of asphaltenes, to determine the variations of solubility index ($\delta$) in connection with variations of the refraction index of known hydrocarbon constituents including light hydrocarbons and of several known reference asphaltenes, to deduce therefrom a correlation relation modelling these variations of solubility index ($\delta$), and to apply this correlation relation to a thermodynamic equilibrium model to directly predict the flocculation threshold of the asphaltenes contained in said hydrocarbon mixture.

4. A device as claimed in claim 3, characterized in that the system comprises a programmed computer (3).

5. A device as claimed in claim 3, characterized in that the system comprises a programmed computer (3) and a device (1) for bringing asphaltenes into solution in a solvent at variable concentrations.

* * * * *